United States Patent
Amthor et al.

(10) Patent No.: US 11,092,659 B2
(45) Date of Patent: Aug. 17, 2021

(54) SUB VOXEL RESOLUTION MAGNETIC RESONANCE FINGERPRINTING IMAGING

(71) Applicant: KONINKLIJKE PHILIPS N.V., Eindhoven (NL)

(72) Inventors: Thomas Erik Amthor, Hamburg (DE); Mariya Ivanova Doneva, Hamburg (DE); Karsten Sommer, Hamburg (DE); Peter Koken, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/498,555

(22) PCT Filed: Mar. 30, 2018

(86) PCT No.: PCT/EP2018/058308
§ 371 (c)(1),
(2) Date: Sep. 27, 2019

(87) PCT Pub. No.: WO2018/178343
PCT Pub. Date: Oct. 4, 2018

(65) Prior Publication Data
US 2020/0041594 A1 Feb. 6, 2020

(30) Foreign Application Priority Data

Mar. 30, 2017 (EP) .................... 17163880

(51) Int. Cl.
*G01R 33/483* (2006.01)
*G01R 33/24* (2006.01)
(Continued)

(52) U.S. Cl.
CPC ....... *G01R 33/4835* (2013.01); *G01R 33/243* (2013.01); *G01R 33/246* (2013.01);
(Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 10,321,845 B2    6/2019  Amthor et al.
2005/0135664 A1*  6/2005  Kaufhold .............. G06T 11/006
                                                                382/131
(Continued)

OTHER PUBLICATIONS

Ma et al "Magnetic Resonance Fingerprinting" Nature, vol. 495 p. 187-193.
(Continued)

*Primary Examiner* — Walter L Lindsay, Jr.
*Assistant Examiner* — Frederick Wenderoth

(57) ABSTRACT

A magnetic resonance imaging (MRI) system (100) includes a memory (134) for storing machine executable instructions (140) and magnetic resonance fingerprinting (MRF) pulse sequence commands (142) which cause the MRI system to acquire MRF magnetic resonance data (144) according to an MRF protocol. The pulse sequence commands are configured for acquiring the MRF magnetic resonance data in two-dimensional slices (410, 412, 414, 416, 418, 420), having a slice selection direction. A train of pulse sequence repetitions includes a sampling event where the MRF data is repeatedly sampled. Execution of the machine executable instructions causes a processor to control the MRI system to: acquire (200) the MRF magnetic resonance data; construct (202) a series (148) of at least one magnetic resonance parameter value for each voxel of the two dimensional slices; and calculate (204) a composition (502, 504, 506, 508) of each of a set of predetermined substances within two or more sub-voxels (306, 308) for each voxel of the two dimensional slices using a sub-voxel magnetic resonance fingerprinting dictionary (150) for each of the two or more
(Continued)

sub-voxels and the series of the at least one magnetic resonance parameter value. Each voxel in the slice selection direction is divided into two or more sub-voxels.

19 Claims, 5 Drawing Sheets

(51) Int. Cl.
*G01R 33/44* (2006.01)
*G01R 33/48* (2006.01)
*G01R 33/56* (2006.01)
*G01R 33/565* (2006.01)

(52) U.S. Cl.
CPC ....... *G01R 33/443* (2013.01); *G01R 33/4828* (2013.01); *G01R 33/5604* (2013.01); *G01R 33/5659* (2013.01); *G01R 33/56563* (2013.01)

(58) Field of Classification Search
USPC ......................................................... 324/309
See application file for complete search history.

(56) References Cited

U.S. PATENT DOCUMENTS

| | | | |
|---|---|---|---|
| 2012/0235678 A1 | 9/2012 | Seiberlich et al. | |
| 2012/0277572 A1* | 11/2012 | Hubbard | A61B 5/055 600/419 |
| 2013/0265047 A1 | 10/2013 | Griswold et al. | |
| 2013/0271132 A1 | 10/2013 | Griswold | |
| 2015/0301138 A1* | 10/2015 | Griswold | G01R 33/4818 324/309 |
| 2015/0346300 A1* | 12/2015 | Setsompop | G01R 33/4828 324/309 |
| 2016/0131727 A1* | 5/2016 | Sacolick | G01R 33/5614 324/318 |
| 2017/0011255 A1 | 1/2017 | Kaditz et al. | |
| 2017/0319097 A1 | 11/2017 | Amthor et al. | |

OTHER PUBLICATIONS

Pauley et al "Parameter Relations for the Sinnar-Le Roux Selective Excitation Pulse Design Algorithm" IEEE Transactions on Medical Imaging, vol. 10 No. 1 p. 53-65 Mar. 1991.
Greenspan et al "MRI Inter-Slice Reconstruction Using Super-Resolution" Magnetic Resonance Imaging, vol. 20, No. 5, Jun. 1, 2002 p. 437-446.
Ropele et al "Super-Resolution MRI Using Microscopic Spatial Modulaton of Magnetization" Proceedings of the International Society for Magnetic Resonance in Med. vol. 18, Apr. 17, 2010 p. 764.
Vu An T et al "Evaluation of Slice Dithered Enhanced Resolution Simultaneous Multislice for Human FMRI" Neuroimage, vol. 164, Feb. 7, 2017 p. 164-171.
Hamilton et al "Magnetic Resonance Fingerprinting With Chemical Exchange for Quantification of Subvoxel T1 . . . " Proceedings of the International Society for Magnetic Resonance in Med. vol. 23, May 15, 2015, p. 329.
Guido Buonincontri et al "MR Fingerprinting With Simultaneous B1 Estimation" Magnetic Reson. in Med. vol. 76, No. 4, Oct. 28, 2015 p. 1127-1135.
International Search Report From PCT/EP2018/058308 dated Jun. 21, 2018.
Jiang et al.,"MR fingerprinting using fast imaging with steady state precession (FISP) with spiral readout" MRM 74, 1621 (2015).
Van Reeth et al., Super-Resolution in Magnetic Resonance Imaging: A Review, Concepts in Magnetic Resonance Part A, 40, 306 (2012).
Ye et al "Accelerating Magnetic Resonance Fingerprinting Using T-Blipped Simultaneous Multislice" Magnetic Resonance in Med. vol. 75, p. 2078-2085 May 2016.
Bilgic et al "Simultaneous multislice magnetic resonance fingerprinting (SMS-MRF) with direct-spiral . . . " Magnetic Resonance in Med. May 2016.
Jiang et al "Use of pattern recognition for unaliasing simultaneously acquired slices in simultaneous multislice MR fingerprinting" Magnetic Resonance in Med. vol. 78, p. 1870-1876 Nov. 2017.

\* cited by examiner

MRF IMAGES

SUB VOXEL RESOLUTION MAGNETIC RESONANCE FINGERPRINTING IMAGING

CROSS REFERENCE TO RELATED APPLICATIONS

This application is a U.S. national phase application of International Application No. PCT/EP2018/058308 filed on Mar. 30, 2018, which claims the benefit of EP Application Serial No. 17163880.2 filed on Mar. 30, 2017 and is incorporated herein by reference.

FIELD OF THE INVENTION

The invention relates to magnetic resonance imaging, in particular to magnetic resonance fingerprinting.

BACKGROUND OF THE INVENTION

Magnetic Resonance fingerprinting (MRF) is a technique where a number of RF pulses, distributed in time, are applied such that they cause signals from different materials or tissues to have a unique contribution to the measured Magnetic Resonance (MR) signal. A limited dictionary of precalculated signal contributions from a set or fixed number of substances is compared to the measured MR signals and within a single voxel the composition can be determined. For example if it is known that a voxel only contains water, fat, and muscle tissue the contribution from these three materials need only be considered and only a few RF pulses are needed to accurately determine the composition of the voxel.

The magnetic resonance fingerprinting technique was introduced in the journal article Ma et al., "Magnetic Resonance Fingerprinting," Nature, Vol. 495, pp. 187 to 193, doi:10.1038/nature 11971. The magnetic fingerprinting technique is also described in United States patent applications US 2013/0271132 A1 and US 2013/0265047 A1.

United States patent application publication US 2017/011255 A1 discloses a system that determines an invariant magnetic-resonance (MR) signature of a biological sample. During operation, the system determines a magnetic-resonance (MR) model of voxels in a biological sample based on differences between MR signals associated with the voxels in multiple scans and simulated MR signals. The MR signals are measured or captured by an MR scanner in the system during multiple MR scans, and based on scanning instructions, and the simulated MR signals for the biological sample are generated using the MR model and the scanning instructions. Moreover, the system iteratively modifies the scanning instructions (including a magnetic-field strength and/or a pulse sequence) in the MR scans based on the differences until a convergence criterion is achieved. Then, the system stores, in memory, an identifier of the biological sample and a magnetic-field-strength-invariant MR signature of the biological sample that is associated with the MR model.

The journal article Pauly et. al., "Parameter relations for the Shinnar-Le Roux selective excitation pulse design algorithm [NMR imaging]," in IEEE Transactions on Medical Imaging, vol. 10, no. 1, pp. 53-65, March 1991, doi: 10.1109/42.75611 discloses a review of the Shinnar-Le Roux method of calculating the flip angle and phase distribution across a slice. This paper describes how to design a pulse that produces a specified slice profile.

SUMMARY OF THE INVENTION

The invention provides for a magnetic resonance imaging system, a computer program product, and a method in the independent claims. Embodiments are given in the dependent claims.

Magnetic resonance fingerprinting has the ability to rapidly and accurately determine the concentration and/or spatial distribution of tissue types, substances of materials within a subject. Examples and embodiments described herein may have the benefit of being able to increase the resolution of magnetic resonance images produced by magnetic resonance fingerprinting to the sub voxel level. This may be accomplished by noting that the flip angle and/or the phase distribution within a two dimensional slice is not uniform in the slice selection direction. Voxels can therefore be divided into sub voxels. The magnetic resonance fingerprinting (MRF) signal for a particular voxel is assumed to be a combination of the MRF signal for each of its sub voxels. This enables magnetic resonance fingerprinting at a sub voxel level.

When producing a magnetic resonance image with a sub voxel resolution it is not necessary to measure the flip angle and/or phase distribution within each slice along the slice direction. This information is already included or encoded in the magnetic resonance fingerprinting dictionary. When performing conventional magnetic resonance fingerprinting, the pulse sequence is specified and the magnetic resonance fingerprinting dictionary is typically calculated using the Bloch equations. It is possible to measure the fingerprints for the dictionary empirically. However, as a practical matter methods which use the Bloch equation work well and yield good results. Embodiments extend the resolution in the slice selection direction by dividing the voxels into two or more sub voxels and then using a fingerprinting dictionary that has entries that have been calculated for each of these two or more sub voxels.

Embodiments use separate dictionary entries for each of the two or more sub voxels that do not assume a uniform excitation pulse profile within the voxel. For each of the two or more sub voxels the excitation pulse profile is divided into distinct parts representing each of the two or more sub voxels. The excitation pulse profile is the flip angle distribution and the phase distribution within a voxel. The excitation pulse profile within each of the two or more sub voxels is straight forward to calculate. This can be done for example using the Shinnar-Le Roux method. The Shinnar-Le Roux method can be applied to the pulse sequence specified in the pulse sequence instructions. In fact, an RF waveform can be chosen to increase the asymmetry of the flip angle distribution and/or phase distribution in the slice selection direction.

The measured magnetic resonance fingerprint for a voxel (referred to herein as the series of at least one magnetic resonance parameter value for each voxel) is a combination of the signals from each of the two or more sub voxels. The composition of the sub voxels is then obtained by solving an optimization problem. The optimization provides a means to combine possible magnetic resonance fingerprint from all of the two or more sub voxels to match the measured magnetic resonance fingerprint for the whole voxel. The result is that the solution of the optimization problem yields a composition for each of the two or more sub voxels.

In one aspect the invention provides for a magnetic resonance imaging system. The magnetic resonance imaging system comprises a memory for storing machine-executable instructions and MRF pulse sequence commands. MRF as used herein is an abbreviation for magnetic resonance fingerprinting. The MRF pulse sequence commands cause the magnetic resonance imaging system to acquire MRF magnetic resonance data according to a magnetic resonance fingerprinting protocol. The pulse sequence commands are configured for acquiring the MRF magnetic resonance data in two-dimensional slices. The two-dimensional slices have a slice selection direction. The slice selection direction is perpendicular to the two-dimensional slices. The pulse sequence commands comprise instructions that are configured for causing a train of pulse sequence repetitions. The train of pulse sequence repetitions comprises a sampling event where the MRF magnetic resonance data is repeatedly sampled.

The magnetic resonance imaging system further comprises a processor for controlling the magnetic resonance imaging system. Execution of the machine-executable instructions causes the processor to acquire the MRF magnetic resonance data by controlling the magnetic resonance imaging system with the MRF pulse sequence commands. Execution of the machine-executable instructions further causes the processor to construct a series of at least one magnetic resonance parameter value for each voxel of the two-dimensional slices using the MRF magnetic resonance data. Each of the series corresponds to the sampling event of each pulse sequence repetition. The magnetic resonance parameter value may be any value which is typically measured and imaged using the magnetic resonance imaging system. In magnetic resonance imaging fingerprinting the MRF magnetic resonance data is not used to directly reconstruct an image from data acquired in the Fourier space. Instead the acquired magnetic resonance data is used to construct a series of intermediate images of each of the magnetic resonance parameters. For example, a proton density weighted image has an amplitude which represents the number of protons per volume or within a voxel. However, the reconstructed image also has a complex part. For constructing a MR fingerprint the amplitude and/or the phase can be used to construct the fingerprint.

As these images are typically under-sampled the image quality is so poor that the image itself may not be usable. However, looking at the value for these images for each voxel a series of data or a vector can be constructed for that particular voxel. This series of data for each voxel may also be referred to herein as the "signal," "signal vector," or "MRF signal."

Using the series of the at least one magnetic resonance parameter value the composition of each voxel can be determined by comparing the series of the magnetic resonance parameter to a magnetic resonance fingerprinting dictionary. The magnetic resonance fingerprinting dictionary may have values which are either simulated or measured empirically for particular substances or tissues. The dictionary can be compared to the series of at least one magnetic resonance parameter value for each of the voxels and compared to the magnetic resonance fingerprinting dictionary to infer which of the set of predetermined substances are within that voxel.

Execution of the machine-executable instructions further cause the processor to calculate a composition of each of a set of predetermined substances within two or more sub-voxels for each voxel of the two-dimensional slices using a sub-voxel magnetic resonance fingerprinting dictionary for each of the two or more sub-voxels and the series of the at least one magnetic resonance parameter value. The sub-voxels may be constructed by dividing voxels in the slice selection direction. This embodiment may be beneficial because the magnetic resonance fingerprinting can be used to identify the contents of a voxel split into sub-voxels. This may provide for a means of increasing the resolution of a conventional magnetic resonance fingerprinting image.

The predetermined substances as used herein may encompass a material such as water or fat. A substance may also be considered to be a type of tissue or identify a type of tissue which is diseased or has a pathology also.

In another embodiment, each of the train of pulse sequence repetitions comprises a radio-frequency pulse chosen from a predetermined distribution of radio-frequency pulses. The predetermined distribution of radio-frequency pulses are configured to cause magnetic spins to rotate to a distribution of flip angles. The sub-voxel magnetic resonance fingerprinting dictionary for each of the two or more sub-voxels is dependent upon the predetermined distribution of flip angles. This embodiment may be beneficial because varying the flip angle during the magnetic resonance fingerprinting may provide for a means of discriminating between material within different sub-voxels of a voxel.

In another embodiment, the distribution of flip angles varies by a range of 30°.

In another embodiment, the distribution of flip angles varies within a range of 70°.

In another embodiment, the distribution of flip angles varies by a range of 110°.

In another embodiment, the distribution of flip angles varies by a range of 150°.

In another embodiment, the distribution of flip angles varies within a range of 180°.

In another embodiment, execution of the machine-executable instructions further causes the processor to calculate the sub-voxel magnetic resonance fingerprinting dictionary. The sub-voxel magnetic resonance fingerprinting dictionary may be calculated using any one of the standard methods of calculating the steady state magnetic resonance fingerprinting dictionary. For example, the dictionary may be calculated by solving the Bloch equation or by performing an extended phase graph calculation.

In another embodiment, the composition of each of the set of predetermined substances within the two or more sub-voxels for each voxel the two-dimensional slice is calculated by determining the contribution from each of the two or more sub-voxels using a linear optimization. This embodiment may be beneficial because it may provide for a straight forward means of calculating the contribution from each of the two or more sub-voxels.

In another embodiment, the composition of each of the set of predetermined substances within the two or more sub-voxels for each voxel of the two-dimensional slices is calculated by finding the largest inner product of the series of the at least one magnetic resonance parameter value and a dictionary of pre-calculated signals. The sub-voxel magnetic resonance fingerprinting dictionary comprises the dictionary of pre-calculated signals. The pre-calculated signals may be values for different substances that are calculated or measured for the same pulse sequence that was used to acquire the MRF magnetic resonance data and then to construct the series of the at least one magnetic resonance parameter value.

The pre-calculated signals may represent linear combinations of sub-voxel signals with different substance choices, weightings, and/or relative phase factors.

In another embodiment, execution of the machine-executable instructions further causes the processor to calculate a global composition image descriptive of a composition of each of a global set of predetermined substances within each voxel of the two-dimensional slices using a global magnetic resonance fingerprinting dictionary. In this embodiment the MRF magnetic resonance data is used to calculate a conventional magnetic resonance fingerprinting imaging or map.

In another embodiment, execution of the machine-executable instructions further cause the processor to identify voxels of interest within the two-dimensional slice using the global composition image and a predetermined criteria. The calculation of the composition of each of the set of predetermined substances within two or more sub-voxels is limited to the voxels of interest. Execution of the machine-executable instructions further causes the processor to refine the global composition image using the two or more sub-voxels of the voxels of interest. This may be considered to be a replacement of some voxels within the global composition image using information from the sub-voxels which are calculated. This may have the benefit of being used to increase the resolution, or even to help identify pathological tissues in different structures.

In another embodiment, the predetermined criteria are configured to identify any one of the following: boundary regions, abnormal tissue, and combinations thereof.

In another embodiment, the region of interest is descriptive of a brain. The abnormal tissue is a tissue lesion type.

In another embodiment, execution of the machine-executable instructions further causes the processor to choose the sub-voxel magnetic resonance fingerprinting dictionary for each of the two or more sub-voxels using the global mapping. For example the algorithm executed by the machine-executable instructions may look at a neighborhood or adjoining voxels and use this to determine which magnetic resonance fingerprinting dictionary to select. For example if a voxel is identified as a boundary between two different tissue types it would make the most sense to select magnetic resonance fingerprinting dictionaries corresponding to these two types of tissues which are adjoining each other.

In another embodiment, the two-dimensional slices are descriptive of a region of interest. Execution of the machine-executable instructions further causes the processor to receive a B0 map of the region of interest. Execution of the machine-executable instructions further causes the processor to correct the series of at least one magnetic resonance parameter value using the B0 map. This for example may be done by including the B0 values in the sub-voxel magnetic resonance fingerprinting dictionaries or by correcting the intermediate images used to make the MRF signal. For example the B0 value could be used to select particular magnetic resonance fingerprinting dictionaries.

In another embodiment, the memory further contains B0 mapping pulse sequence commands. Execution of the machine-executable instructions further cause the processor to receive the B0 map by acquiring B0 mapping magnetic resonance data by controlling the magnetic resonance imaging system with the B0 mapping pulse sequence commands and then reconstructing the B0 map. The B0 mapping pulse sequence commands in analysis may be constructed according to any magnetic resonance imaging technique that is able to measure and then calculate the B0 map. This for example could be done by measuring the phase difference between two different scans with a difference in the echo time.

In another embodiment, execution of the machine-executable instructions further cause the processor to receive a B1 map of the region of interest. Execution of the machine-executable instructions further causes the processor to correct the series of at least one magnetic resonance parameter value using the B1 map. This for example may be performed by providing the sub-voxel magnetic resonance fingerprinting dictionaries which are dependent upon the B1 value or by using the B1 map to correct any intermediate images used to construct the MRF signal.

In another embodiment, the memory further contains B1 mapping pulse sequence commands which may be used for mapping the B1 value. Execution of the machine-executable instructions further cause the processor to receive the B1 map by acquiring B1 mapping magnetic resonance data by controlling the magnetic resonance imaging system with the B1 mapping pulse sequence commands and then reconstructing the B1 map. The B1 mapping may be performed according to any magnetic resonance imaging technique which is able to map the B1 or excitation field. For example the dual TR method, the saturated double angle method (SDAM), or a phase-sensitive method may be used to measure the B1 map.

In another embodiment, the sub-voxel magnetic resonance fingerprinting dictionary comprises separate entries for different B1 values. For example the B1 map can be used to select entries that correspond to a particular B1 or excitation field value.

In another embodiment, the B1 map is determined using a B1 map encoded magnetic resonance fingerprinting dictionary. This may be considered to be a conventional magnetic resonance fingerprinting dictionary that encodes B1 values. For example the B1 map encoded magnetic resonance fingerprinting dictionary uses the MRF magnetic resonance data to first determine the B1 map on a per voxel basis. This B1 map could then be used by as an input to the sub-voxel magnetic resonance fingerprinting dictionary that comprises separate entries for different B1 values.

In another embodiment, the two or more sub-voxels are two sub-voxels.

In another embodiment, the two or more sub-voxels are three sub-voxels.

In another embodiment, the two or more sub-voxels are four sub-voxels.

In another embodiment, the at least one magnetic resonance parameter is any one of the following: phase, amplitude, and combinations thereof.

In another aspect, the invention provides for a computer program product comprising machine-executable instructions for execution by a processor controlling the magnetic resonance imaging system. Execution of the machine-executable instructions causes the processor to acquire MRF magnetic resonance data by controlling the magnetic resonance imaging system with MRF pulse sequence commands. The MRF pulse sequence commands cause the magnetic resonance imaging system to acquire the MRF magnetic resonance data according to a magnetic resonance fingerprinting protocol. The pulse sequence commands are configured for acquiring the MRF magnetic resonance data in two-dimensional slices. The two-dimensional slices have a slice selection direction. The pulse sequence commands comprise a train of pulse sequence repetitions. The train of pulse sequence repetitions comprises a sampling event where the MRF magnetic resonance data is repeatedly sampled. Execution of the machine-executable instructions further cause the processor to construct a series of at least one magnetic resonance parameter value for each voxel of the two-dimensional slices using the MRF magnetic resonance data. Each of the series corresponds to the sampling event of each pulse sequence repetition.

Execution of the machine-executable instructions further cause the processor to calculate a composition of each of a set of predetermined substances within two or more sub-voxels for each voxel of the two-dimensional slices using a sub-voxel magnetic resonance fingerprinting dictionary for each of the two or more sub-voxels and the series of the at least one magnetic resonance parameter value.

In another aspect, the invention provides for a method of operating the magnetic resonance imaging system. The method comprises acquiring MRF magnetic resonance data by controlling the magnetic resonance imaging system with the MRF pulse sequence commands. The MRF pulse sequence commands cause the magnetic resonance imaging system to acquire the MRF magnetic resonance data according to a magnetic resonance fingerprinting protocol. The pulse sequence commands are configured for acquiring the MRF magnetic resonance data in two-dimensional slices. The two-dimensional slices have a slice selection direction. The pulse sequence commands comprise a train of pulse sequence repetitions. The train of pulse sequence repetitions comprises a sampling event where the MRF magnetic resonance data is repeatedly sampled. The method further comprises constructing a series of at least one magnetic resonance parameter value for each voxel of the two-dimensional slices using the MRF magnetic resonance data. Each of the series corresponds to the sampling event of each pulse sequence repetition. The method further comprises calculating a composition of each of the set of predetermined substances within two or more sub-voxels for each voxel of the two-dimensional slices using a sub-voxel magnetic resonance fingerprinting dictionary for each of the two or more sub-voxels and the series of the at least one magnetic resonance parameter value.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks.

The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Preliminary magnetic resonance data is an example of medical imaging data. A Magnetic Resonance (MR) image is defined herein as being the reconstructed two or three dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
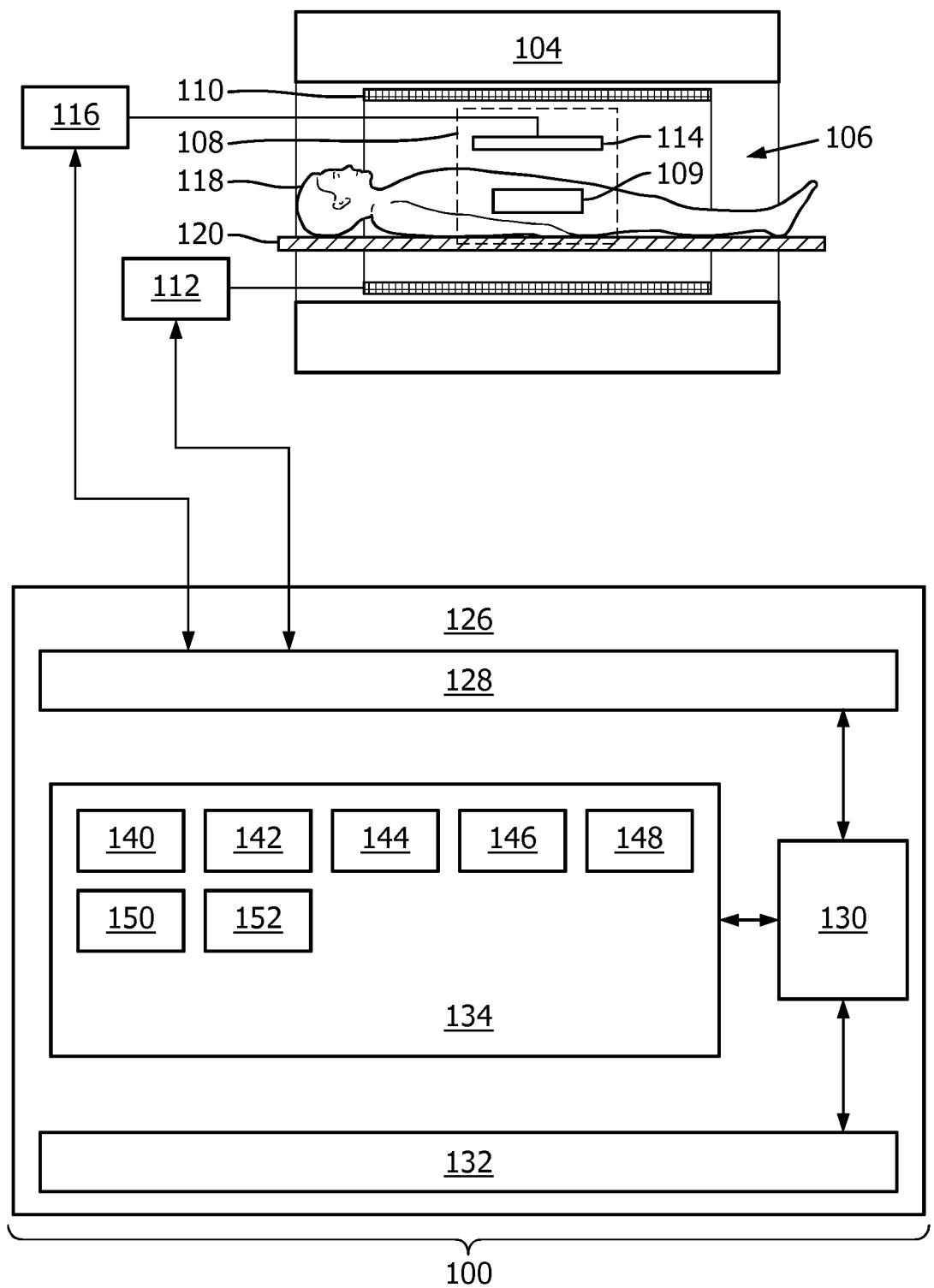
FIG. 1 illustrates and example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

The transceiver 116 and the gradient controller 112 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 130 may be considered to be a non-transitory computer-readable medium.

The memory 134 is shown as containing machine-executable instructions 140 that enable the processor 130 to send and receive commands in order to control the operation and function of the magnetic resonance imaging system 100. The memory 134 is further shown as containing MRF pulse sequence commands 142. The MRF pulse sequence commands are pulse sequence commands that are configured for controlling the magnetic resonance imaging system 100 to acquire or sample magnetic resonance data using a magnetic resonance fingerprinting protocol. The memory 134 is further shown as containing MRF magnetic resonance data 144. The MRF magnetic resonance data is magnetic resonance data that was acquired by controlling the magnetic resonance imaging system 100 with the MRF pulse sequence commands. The memory 134 is further shown as containing intermediate image data 146. The intermediate image data 146 could for example be either phase or amplitude images that are reconstructed from individual samples of the MRF magnetic resonance data. Data from a series of these intermediate image data 146 may be used to construct the series or vector containing 148 containing a measured magnetic resonance parameter for a single voxel. 148 is essentially the magnetic resonance fingerprint for a particular voxel using the MRF pulse sequence commands 142.

The memory 134 is further shown as containing a collection of sub-voxel magnetic resonance fingerprinting dictionaries 150. The magnetic resonance fingerprint 148 can be compared to the sub-voxel magnetic resonance fingerprinting dictionaries 150 to determine the contents of a voxel on a sub-voxel level in the slice selection direction. The memory 152 is further shown as containing values which represent the composition of sub-voxels that were calculated using the series 148 and several sub-voxel magnetic resonance fingerprinting dictionaries. This may for example be applied to the entire magnetic resonance fingerprinting and the resolution for the magnetic resonance fingerprinting images can be calculated at a higher resolution in the slice selection direction. Otherwise the MRF magnetic resonance data 144 can be used to calculate a conventional magnetic resonance fingerprinting image and the values of some sub-voxels selected from this image can be replaced with the values 152.

Figure 2:
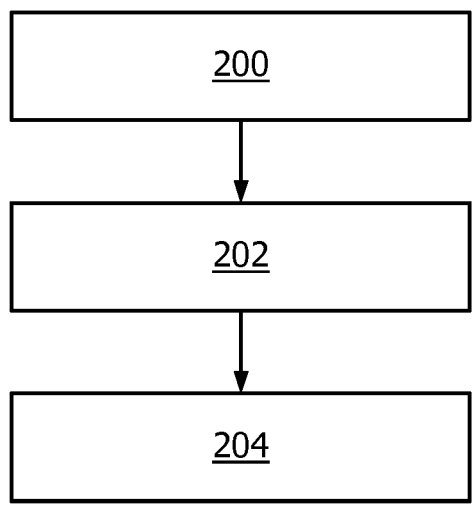
FIG. 2 shows a flow chart which illustrates an example of a method of operating the magnetic resonance imaging system of FIG. 1.

FIG. 2 shows a flowchart which illustrates a method of operating the magnetic resonance imaging system 100 of FIG. 1. First in step 200 the magnetic resonance imaging system 100 is controlled with the MRF pulse sequence commands 142. This causes the magnetic resonance imaging system 100 to acquire the MRF magnetic resonance data 144. Next in step 202 the processor 130 is controlled so that it constructs a series of at least one magnetic resonance parameter value 148 for each voxel of two-dimensional slices using the MRF magnetic resonance data. Each of the series corresponds to the sampling event of each pulse sequence repetition. Then finally in step 204 a composition of each of a set of predetermined substances within two or more sub-voxels for each voxel of the two-dimensional slices is calculated using a sub-voxel magnetic resonance fingerprinting dictionary 150 and the series 148 containing the measured magnetic resonance parameter.

Magnetic Resonance Fingerprinting (MRF) is new acquisition and reconstruction technique in the field of Magnetic Resonance Imaging (MRI). Instead of acquiring data for a given set of sequence parameters, which results in images with predefined contrast, MRF collects data for a whole range of different sequence parameters. The resulting fingerprint is matched with a dictionary of signal evolutions precomputed from characteristic tissue parameters, resulting in their simultaneous estimation.

The spatial resolution in slice-selection direction of all commonly used multi-slice 2D MR imaging methods is limited to the slice width. Super-resolution methods exist, but require the acquisition of additional overlapping slices.

The proposed method overcomes this limitation by exploiting the shape of the excitation pulse profile and by using MR Fingerprinting to identify the constituents of spatially distinct parts of the slice width. It enables the reconstruction of images with intra-slice spatial resolution without the need for slice overlap or additional measurements. The method can be applied retrospectively to standard MRF measurements.

Examples may have one or more of the following features:
1. A modified MRF dictionary calculation method: Dictionary entries are calculated by integrating over distinct parts of the excitation pulse profile.
2. A modified MRF reconstruction method: For each voxel, the contributions of fingerprints belonging to the different parts of the slice profile are determined by solving an optimization problem.

Figure 3:
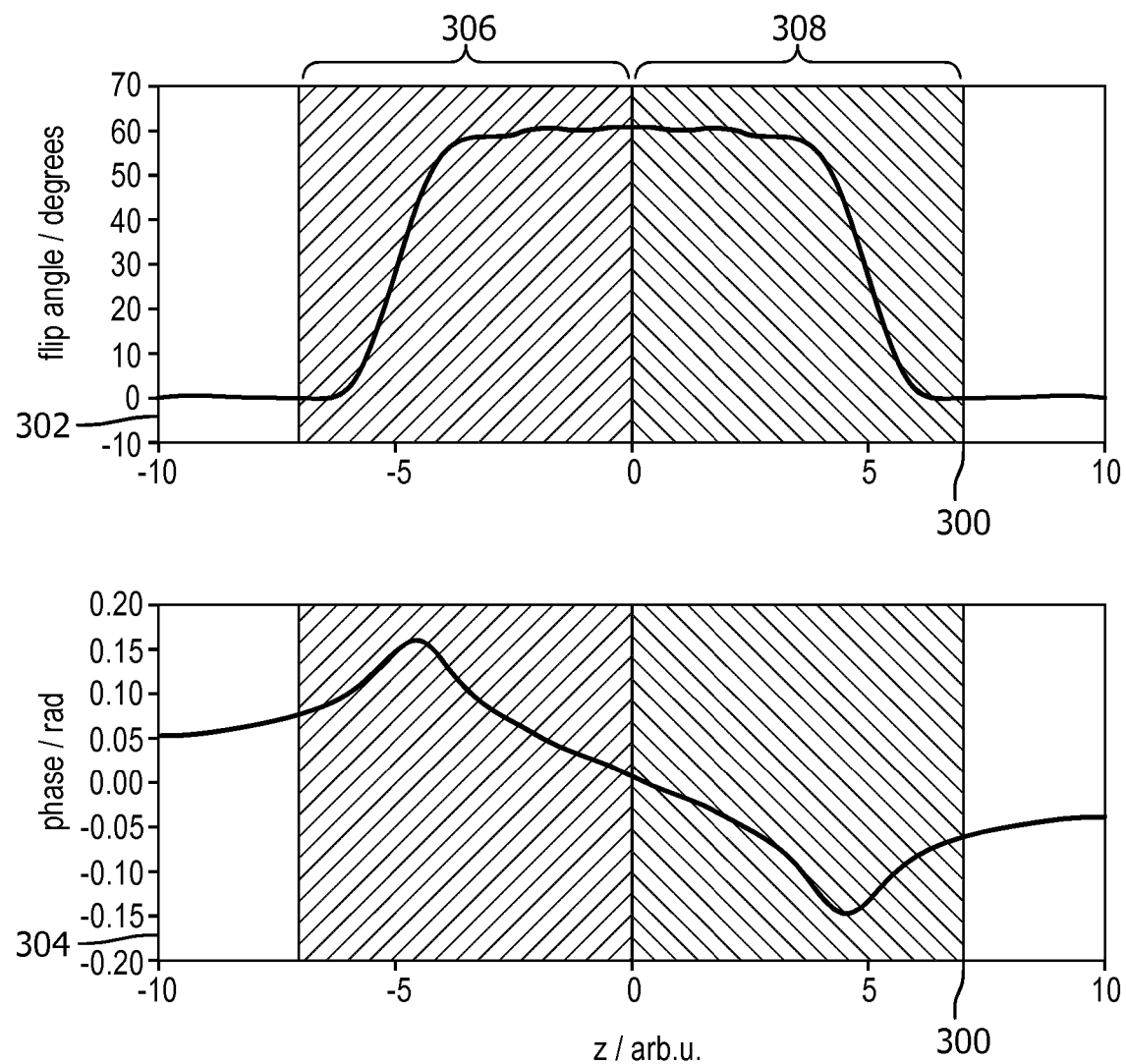
FIG. 3 shows a plot of the flip angle and phase distribution within a slice for a 60-degree RF pulse.

In one example a method for creating the sub-slice fingerprints comprises one or more of the following steps:
1. The RF flip angle and RF phase slice profiles are calculated for each excitation pulse used in the fingerprint train. FIG. 3 shows an example for a 60-degree pulse.
2. The slice profiles are divided into N sub-slices. In FIG. 3, a set of N=2 sub-slices is indicated by the hatched regions.
3. For each substance to be contained in the fingerprint dictionary, separate fingerprints are calculated for each sub-slice by summing up the signal responses for all flip angle and phase combinations within that sub-slice. In the example in FIG. 3, this can be achieved by sampling several points within each hatched region and calculating the sub-slice fingerprint as the sum of all fingerprints belonging to the region.

The exact shape of the flip angle and phase slice profile depends on the RF pulse intensity. For low flip angles, the profiles are almost rectangular, while for high flip angles the profiles are distorted. Since the exact shape is included in the calculations, it can be beneficial to include both small and large flip angles in the fingerprint train to increase distinguishability of the signal responses from different spatial regions.

FIG. 3 illustrates one means of constructing a magnetic resonance fingerprint with sub-voxel resolution. There are two charts. The X-axis in both charts is in the slice selection direction 300. FIG. 3 shows the flip angle 302 and the phase angle distribution 304 through a slice for a 60° RF pulse. The flip angle distribution is symmetric, however the phase distribution is anti-symmetric. This makes the signal responses from the sub-slices with Z<0 differ from those with Z>0. The area labeled 306 corresponds to the region of the first sub-voxel 306 and the region 308 corresponds to the region of the second sub-voxel. It can be seen that within the two sub-voxel regions the phase is significantly different. This enables a separate magnetic resonance fingerprinting dictionary to be constructed for each region 306 and 308 which enables a sub-voxel resolution. Normally radio-frequency pulses are selected so that they have a square or symmetric shape. The radio-frequency pulse could for example be altered so that it no longer has a symmetric appearance as it does in the chart plotting 300 versus 302. This can enable dividing the voxel into even more than two regions. For the particular example shown in FIG. 3 the phase may be used to differentiate the voxels on a sub-voxel resolution. However, this is dependent upon the phase 304. Errors in the B0 field may for example cause inaccuracies.

In the case of N=2 sub-slices (as is shown in FIG. 3), two fingerprints of the same substance differ only in phase, not in amplitude. If more than two sub-slices are used, then also the amplitude distributions of the sub-slice fingerprints differ.

Below, a method of sub-slice reconstruction is discussed. In this example, the measured signal is assumed to be a linear combination of the fingerprints from the different spatial regions.

The matching problem could be solved in different ways. One way is to write it in terms of a linear optimization problem, minimize $\|D^T x - s\|_2$ subject to $x_i \geq 0$, where D is a complex-valued dictionary containing all fingerprints of all sub-slices, s is the measured complex-valued signal, and x is the vector of component abundancies. If individual phase factors need to be considered (which is the case for SSFP-based MRF sequences with $B_0$ variations in the imaging volume), the minimization problem will have to be adapted. A known $B_0$ map could be used to eliminate a constant phase factor in the fingerprint signal s before matching. If different phase factors are expected for the different sub-slices, then the relative phase may be included as an additional optimization parameter. In this case, the following method may be better suited.

This second method is explained for the case of two sub-slices, with each sub-voxel containing only one substance, but it could easily be extended to more sub-slices and components. Since this method allows restriction to a fixed number of constituents, it should in general allow a more stable solution.

For each voxel, all possible combinations of sub-voxel constituents for a fixed number of density ratios and relative phases are tested, and the best combination is found by comparing the inner products with the measured signal.

Let n be the number of substances considered in the dictionary. Then we have n fingerprints for each sub-slice. For the two sub-slices, we could create two sub-dictionaries $D^{(1)}$ and $D^{(2)}$ containing the respective fingerprints.

For each combination of substances a and b, ratios $\varepsilon$, and relative phase factors $\varphi$, the expected signal can be expressed as $$S(a,b,\varepsilon,\varphi) = \varepsilon D_a^{(1)} + (1-\varepsilon) e^{i\varphi} D_b^{(2)},$$

and the best match for a measured signal s can be found by choosing the set of parameters that leads to the maximum the inner product of the normalized signal vectors, $$(a^{opt}, b^{opt}, \varepsilon^{opt}, \varphi^{opt}) = \operatorname*{argmax}_{(a,b,\varepsilon,\varphi)} \frac{\langle S(a,b,\varepsilon,\varphi), s \rangle}{\|S(a,b,\varepsilon,\varphi)\| \|s\|}.$$

The optimized fingerprint indices $a^{opt}$ and $b^{opt}$ are then used to create maps with double resolution in slice-selection direction. The relative proton densities of the constituents in the two sub-voxels are given by $$PD_a \propto \varepsilon^{opt} \frac{\|s\|}{\|S(a^{opt}, b^{opt}, \varepsilon^{opt}, \varphi^{opt})\|} \text{ and}$$

$$PD_b \propto (1-\varepsilon^{opt}) \frac{\|s\|}{\|S(a^{opt}, b^{opt}, \varepsilon^{opt}, \varphi^{opt})\|}.$$

Figure 4:
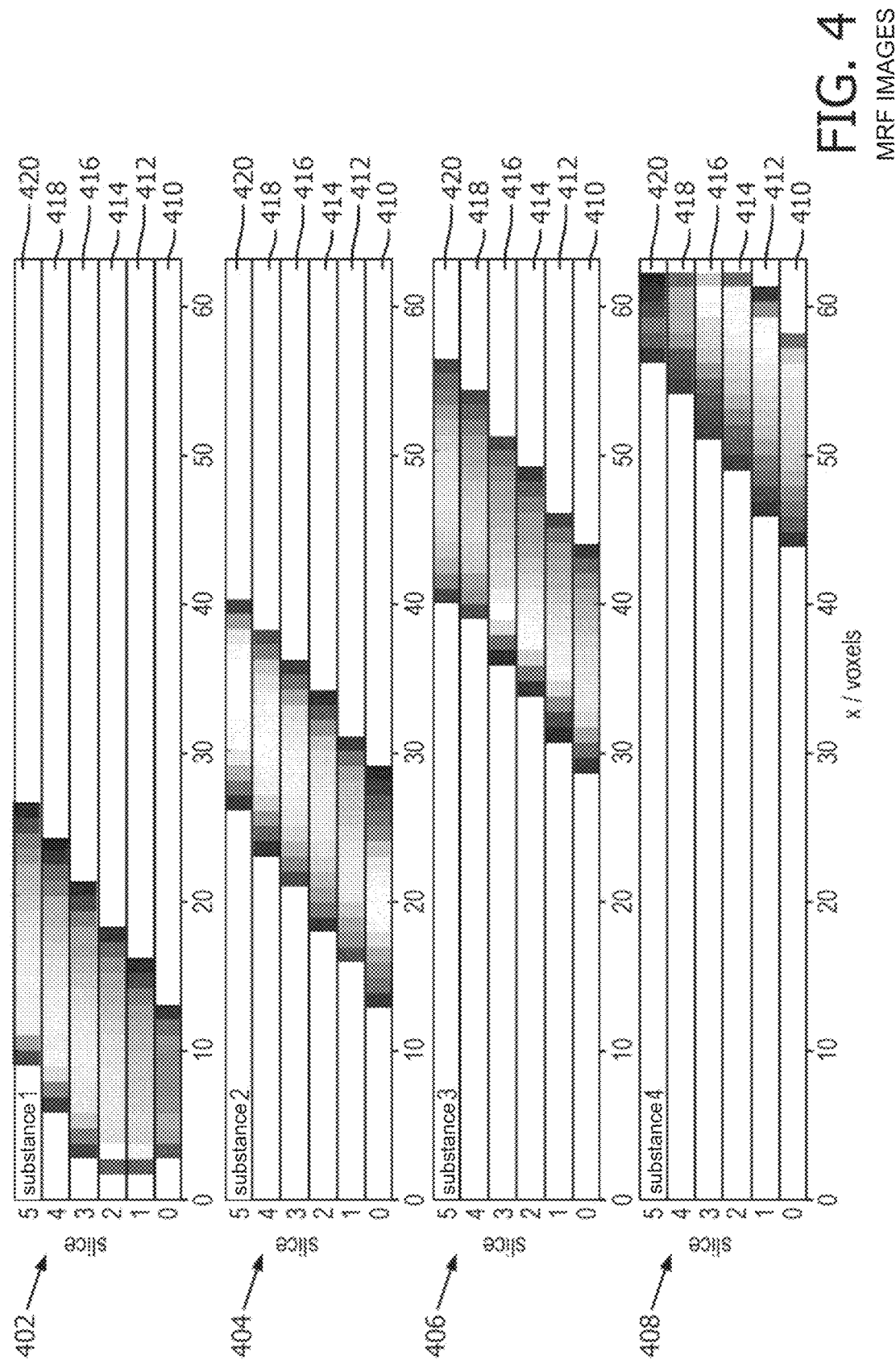
FIG. 4 shows a mapping of the concentration four substances using conventional magnetic resonance fingerprinting.

FIG. 4 shows conventional magnetic resonance fingerprint images that were reconstructed. To construct these images four known gel samples containing different substances were tilted with respect to a region of interest that was divided into parallel slices. The image 402 images substance 1, image 404 images substance 2, image 406 images substance 3, and image 408 images substance 4.

Each image is from voxels within six distinct slices. Slice 0 is indicated by 410, slice 1 is labeled as 412, slice 2 is labeled as 414, slice 3 is labeled as 416, slice 4 is labeled as 418, slice 5 is labeled as 420. In these four images, 402, 404, 406, 408, the same data was used.

Figure 5:
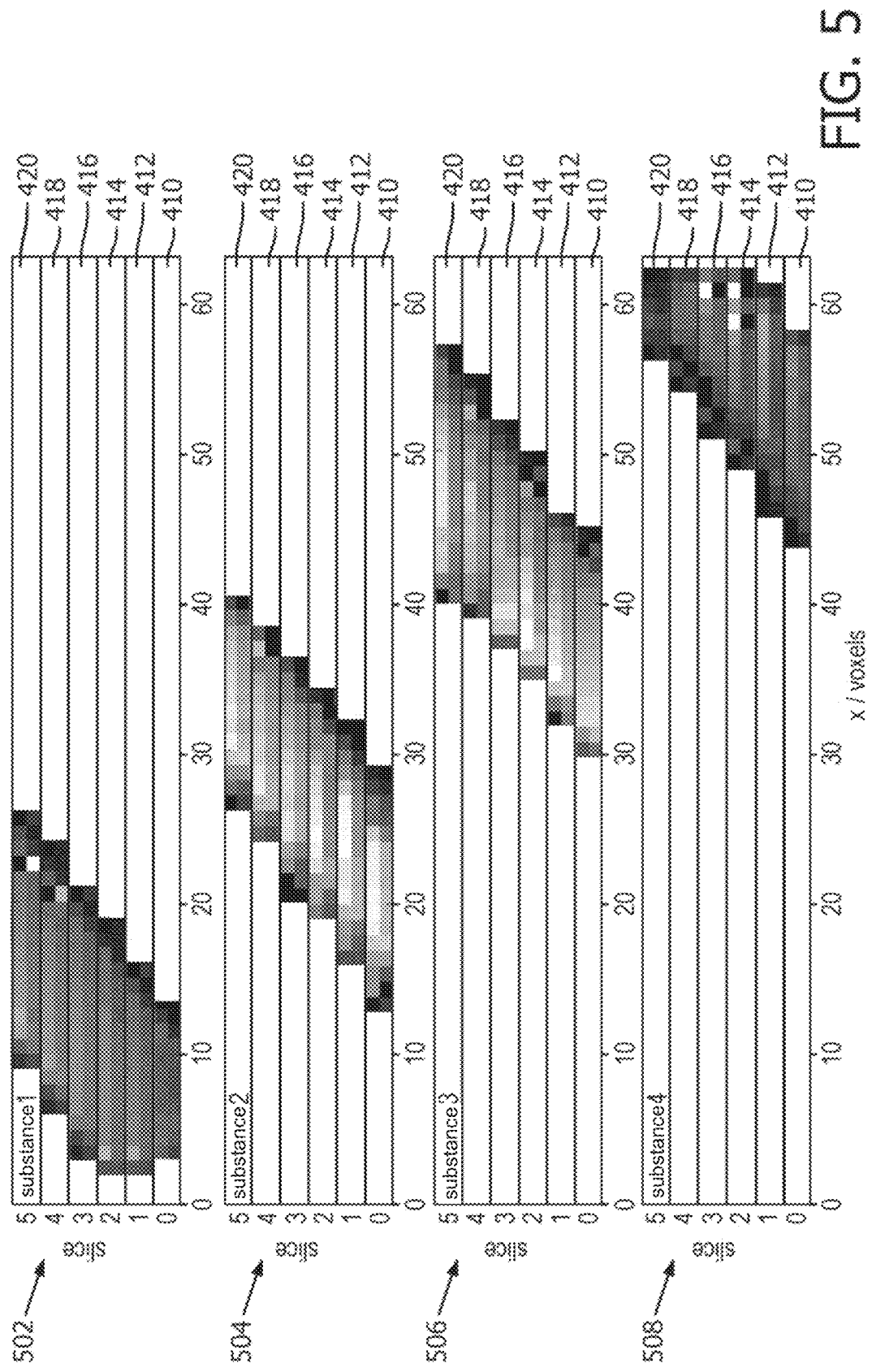
FIG. 5 shows a mapping of the concentration four substances using magnetic resonance fingerprinting with sub voxel resolution.

FIG. 5 shows four additional images that were reconstructed using the same magnetic resonance fingerprinting dictionary but with using sub-voxel magnetic resonance fingerprinting dictionaries. Matching was performed using an MRF dictionary containing eight fingerprints for four substances with two sub-slice fingerprints each. The algorithm described above was employed with 21 possible values for $\epsilon$ and 30 possible values for $\varphi$.

Image 502 corresponds to image 402, image 504 corresponds to image 404, image 506 corresponds to image 406, image 508 corresponds to image 408. In comparing FIGS. 4 and 5 it can be seen that the location of each of the substances was identified equally in both images. In FIG. 5 the gel samples are imaged at a higher resolution.

In FIG. 5 it can be seen that there are some variations where voxels on one side of the slice are consistently brighter or more intense than voxels on the other side. These may be possibly due to B1+ or possibly even B0 effects. When there is a gradient of these fields across a voxel the resulting effect on the sub-voxel signals may look similar to an uneven density distribution of the substance. The example shown in FIG. 5 does not take into account corrections for the B1 or B0 field. The effect shown in this image could be minimized by using for example lower magnetic field strengths. In the example shown in FIG. 5 a field strength of 3 T was used. If a field strength of 1.5 T or less was used this effect may be minimized. The effect may also be minimized by considering the field gradient effects more accurately in the calculations, using a completely asymmetric slice profile, or measuring the B0 and B1 maps and taking into account these effects in the sub-voxel signal calculation.

As an example, a set of four known gel samples has been imaged using a multi-slice acquisition with four slices of 8 mm width. The MR Fingerprinting sequence used is our standard MRF sequence, using a spoiled SSFP implementation. The samples, contained in thin-walled glass tubes, were placed next to each other and were rotated with respect to the slice-selection direction so that the spatial resolution can be observed at the edges between the samples. The partial-volume abundances (densities) of the individual substances as derived from the sub-slice analysis are shown in FIG. 5. The edges of the individual tubes are well resolved.

In another example, a standard MRF matching is performed first to create standard-resolution parameter maps. From these maps, the constituents in and around a region of interest (e.g., a lesion in the brain) can be determined. The described method to increase spatial resolution can then be performed locally in the region of interest. The dictionary used for spatial optimization can be restricted to the known constituents of the region, thereby enabling a fast and stable calculation.

In another example, the RF pulse is designed in such a way, that the RF and phase profile are asymmetric, in order to increase the distinguishability of the sub-slice signals.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
126 computer system
128 hardware interface
130 processor
132 user interface
134 computer memory
140 machine executable instructions
142 MRF pulse sequence commands
144 MRF magnetic resonance data
146 intermediate image data
148 series or vector containing a measured magnetic resonance parameter for a single voxel
150 collection of sub-voxel magnetic resonance fingerprinting dictionaries
152 values representing composition of sub-voxels
200 acquire MRF magnetic resonance data by controlling the magnetic resonance imaging system with the MRF pulse sequence commands
202 construct a series of at least one magnetic resonance parameter value for each voxel of the two dimensional slices using the MRF magnetic resonance data
204 calculate a composition of each of a set of predetermined substances within two or more sub voxels for each voxel of the two dimensional slices using a sub-voxel magnetic resonance fingerprinting dictionary for each of the two or more sub voxels and the series of the at least one magnetic resonance parameter value
300 distance in slice selection direction
302 flip angle [degrees]
304 phase [radians]
306 region of first sub voxel
308 region of second sub voxel
402 magnetic resonance fingerprinting image of substance 1
404 magnetic resonance fingerprinting image of substance 2
406 magnetic resonance fingerprinting image of substance 3

408 magnetic resonance fingerprinting image of substance 4
410 slice 0
412 slice 1
414 slice 2
416 slice 3
418 slice 4
420 slice 5
502 sub-voxel magnetic resonance fingerprinting image of substance 1
504 magnetic resonance fingerprinting image of substance 2
506 magnetic resonance fingerprinting image of substance 3
508 magnetic resonance fingerprinting image of substance 4

The invention claimed is:

1. A magnetic resonance imaging system comprising:
a memory for storing machine executable instructions and magnetic resonance fingerprinting (MRF) pulse sequence commands, wherein the MRF pulse sequence commands cause the magnetic resonance imaging system to acquire MRF magnetic resonance data according to an MRF protocol, wherein the pulse sequence commands are configured for acquiring the MRF magnetic resonance data in two dimensional slices, wherein the two dimensional slices have a slice selection direction, wherein the pulse sequence commands comprises a train of pulse sequence repetitions, wherein the train of pulse sequence repetitions comprises a sampling event where the MRF magnetic resonance data is repeatedly sampled;
a processor for controlling the magnetic resonance imaging system, wherein execution of the machine executable instructions causes the processor to:
acquire the MRF magnetic resonance data by controlling the magnetic resonance imaging system with the MRF pulse sequence commands; and
construct a series of at least one magnetic resonance parameter value for each voxel of the two-dimensional slices using the MRF magnetic resonance data, wherein each of the series corresponds to the sampling event of each pulse sequence repetition; and
calculate a composition of each of a set of predetermined substances within two or more sub-voxels of each voxel of the two dimensional slices using a sub-voxel magnetic resonance fingerprinting dictionary for each of the two or more sub-voxels and the series of the at least one magnetic resonance parameter value, wherein sub-voxels divide each voxel in the slice selection direction, wherein each sub-voxel magnetic resonance fingerprinting dictionary comprises separate fingerprints calculated by integrating over distinct parts of an excitation pulse profile for each of the two or more sub-voxels, wherein the excitation pulse profile is a flip angle distribution and a phase angle distribution, wherein the composition within the two or more sub-voxels is calculated by determining the contribution from each of the two or more sub-voxels using linear optimization wherein any one of the following:
the excitation pulse profile has a symmetric flip angle distribution and has an anti-symmetric phase distribution;

the pulse sequence commands specify a radiofrequency pulse, wherein the radio-frequency pulse is asymmetric; and
combinations thereof.

2. A non-transitory computer-readable program product comprising machine executable instructions for execution by a processor controlling a magnetic resonance imaging system, wherein execution of the machine executable instructions causes the processor to:
acquire magnetic resonance fingerprinting (MRF) data by controlling the magnetic resonance imaging system with MRF pulse sequence commands, wherein the MRF pulse sequence commands cause the magnetic resonance imaging system to acquire the MRF data according to a magnetic resonance fingerprinting protocol, wherein the pulse sequence commands are configured for acquiring the MRF data in two dimensional slices, wherein the two dimensional slices have a slice selection direction, wherein the pulse sequence commands comprises a train of pulse sequence repetitions, wherein the train of pulse sequence repetitions comprises a sampling event where the MRF data is repeatedly sampled; and
construct a series at least one magnetic resonance parameter value for each voxel of the two-dimensional slices using the MRF data, wherein each of the series corresponds to the sampling event of each pulse sequence repetition; and
calculate a composition of each of a set of predetermined substances within two or more sub-voxels for each voxel of the two-dimensional slices using a sub-voxel MRF dictionary for each of the two or more sub-voxels and the series of the at least one magnetic resonance parameter value, wherein the sub-voxels divide each voxel in the slice selection direction, wherein the sub-voxel MRF dictionary comprises separate fingerprints calculated by integrating over distinct parts of an excitation pulse profile for each of the two or more sub-voxels, wherein the composition within the two or more sub-voxels is calculated by determining the contribution from each of the two or more sub-voxels using linear optimization; and
wherein any one of the following:
the excitation pulse profile has a symmetric flip angle distribution and has an anti-symmetric phase distribution,
the pulse sequence commands specify a radio-frequency pulse, wherein the radio-frequency pulse is asymmetric, and
combinations thereof.

3. A method of operating a magnetic resonance imaging system, wherein the method comprises:
acquiring magnetic resonance fingerprinting (MRF) magnetic resonance data by controlling the magnetic resonance imaging system with MRF pulse sequence commands, wherein the MRF pulse sequence commands cause the magnetic resonance imaging system to acquire the MRF magnetic resonance data according to a magnetic resonance fingerprinting protocol, wherein the pulse sequence commands are configured for acquiring the MRF magnetic resonance data in two dimensional slices, wherein the two dimensional slices have a slice selection direction, wherein the pulse sequence commands comprises a train of pulse sequence repetitions, wherein the train of pulse sequence repetitions comprises a sampling event where the MRF magnetic resonance data is repeatedly sampled; and constructing a series of at least one magnetic resonance parameter value for each voxel of the two-dimensional slices using the MRF magnetic resonance data, wherein each of the series corresponds to the sampling event of each pulse sequence repetition; and calculating a composition of each of a set of predetermined substances within two or more sub-voxels for each voxel of the two dimensional slices using a sub-voxel magnetic resonance fingerprinting dictionary for each of the two or more sub-voxels and the series of the at least one magnetic resonance parameter value, wherein sub-voxels divide each voxel in the slice selection direction, wherein the sub-voxel magnetic resonance fingerprinting dictionary comprises separate fingerprints calculated by integrating over distinct parts of an excitation pulse profile for each of the two or more sub-voxels, wherein the composition within the two or more sub-voxels is calculated by determining the contribution from each of the two or more sub-voxels using linear optimization wherein any one of the following:

the excitation pulse profile has a symmetric flip angle distribution and has an anti-symmetric phase distribution;

the pulse sequence commands specify a radio-frequency pulse, wherein the radio-frequency pulse is asymmetric; and combinations thereof.

4. The magnetic resonance imaging system of claim 1, wherein each of the train of pulse sequence repetitions comprises a radio frequency pulse chosen from a predetermined distribution of radio frequency pulses, wherein the predetermined distribution of radio frequency pulses are configured to cause magnetic spins to rotate to a distribution of flip angles, wherein the sub-voxel magnetic resonance fingerprinting dictionary for each of the two or more sub-voxels is dependent upon the predetermined distribution of flip angles.

5. The magnetic resonance imaging system of claim 4, wherein the distribution of flip angles varies by any one of the following: within a range of 30 degrees, within a range of 70 degrees, within a range of 110 degrees, within a range of 150 degrees, and within a range of 180 degrees.

6. The magnetic resonance imaging system of claim 1, wherein execution of the machine executable instructions causes the processor to calculate a composition image descriptive of a composition of each of a set of predetermined substances within each voxel of the two dimensional slices using an MRF dictionary.

7. The magnetic resonance imaging system of claim 6, wherein execution of the machine executable instructions further causes the processor to:

identify voxels of interest within the two-dimensional slices using the composition image and a predetermined criteria, wherein the calculation of the composition of each of the set of predetermined substances within two or more sub-voxels is limited to the voxels of interest; and refine the composition image using the two or more sub-voxels of the voxels of interest.

8. The magnetic resonance imaging of claim 7, wherein the predetermined criteria are configured to identify any one of the following:

boundary regions, abnormal tissue, and combinations thereof.

9. The magnetic resonance imaging system of claim 7, wherein execution of the machine executable instructions further causes the processor to choose the sub-voxel magnetic resonance fingerprinting dictionary for each of the two or more sub-voxels using the composition image.

10. The magnetic resonance imaging system of claim 1, wherein the two-dimensional slices are descriptive of a region of interest, wherein execution of the machine executable instructions further causes the processor to receive a B0 map of the region of interest, wherein execution of the machine executable instructions further causes the processor to correct the series of at least one magnetic resonance parameter value using the B0 map.

11. The magnetic resonance imaging system of claim 10, wherein the memory further contains B0 mapping pulse sequence commands, wherein execution of the machine executable instructions further causes the processor to receive the B0 map by:

acquire B0 mapping magnetic resonance data by controlling the magnetic resonance imaging system with the B0 mapping pulse sequence commands; and reconstruct the B0 map.

12. The magnetic resonance imaging system of claim 10, wherein execution of the machine executable instructions further causes the processor to receive a B1 map of the region of interest, wherein execution of the machine executable instructions further causes the processor to correct the series of at least one magnetic resonance parameter value using the B1 map.

13. The magnetic resonance imaging system of claim 1, wherein the at least one magnetic resonance parameter value is any one of the following: phase, amplitude, and combinations thereof.

14. The magnetic resonance imaging system of claim 1, wherein each two-dimensional slice is a single voxel thick.

15. The magnetic resonance imaging system of claim 1, wherein each voxel of each two-dimensional slice is subdivided in the slice select direction into the two or more sub-voxels.

16. The magnetic resonance imaging system of claim 1, wherein each voxel is subdivided into two or more sub-voxels in the slice select direction based on the anti-symmetric phase distribution.

17. The magnetic resonance imaging system of claim 1, wherein the voxels of each two-dimensional slice are divided in the slice select direction into a plurality of sub-voxels using at least one of the anti-symmetric phase distribution and the asymmetric radio frequency pulse to differentiate among the plurality of sub-voxels.

18. The method of claim 3, further including differentiating the two or more sub-voxels of each voxel of each two-dimensional slice based on any one of the anti-symmetric phase distribution, the asymmetric radio frequency pulse, and combinations thereof.

19. The method of claim 3, wherein the contribution from one of the sub-voxels corresponds to the portion of the sampling event during a phase distribution of a first polarity of the excitation profile and a contribution from a second of the sub-voxels corresponds to a portion of the sampling event during a second asymmetric phase distribution of the excitation profile.

* * * * *